United States Patent [19]

Sakai et al.

[11] 4,420,548
[45] Dec. 13, 1983

[54] ELECTROPHOTOGRAPHIC MEMBER WITH HYDRAZONE OR KETAZINE COMPOUNDS

[75] Inventors: Kiyoshi Sakai, Mitaka; Minoru Mabuchi; Toshiko Suzuki, both of Tokyo; Yuji Egarashi, Hino; Shozo Ishikawa, Sayama, all of Japan

[73] Assignee: Canon Kabushiki Kaisha, Tokyo, Japan

[21] Appl. No.: 321,673

[22] Filed: Nov. 16, 1981

[30] Foreign Application Priority Data

Nov. 28, 1980 [JP] Japan .................................. 55-166560
Jul. 23, 1981 [JP] Japan .................................. 56-115483

[51] Int. Cl.³ .......................... G03G 5/06; G03G 5/14
[52] U.S. Cl. ...................................... 430/59; 430/56; 430/70; 430/71; 430/72; 430/73; 430/74; 430/76; 430/77; 430/78; 430/79; 564/249; 564/250; 564/251
[58] Field of Search ....................... 430/56, 58, 59, 70, 430/71, 72, 73, 74, 75, 76, 77, 78, 79; 564/249, 250, 251

[56] References Cited

U.S. PATENT DOCUMENTS

| | | | |
|---|---|---|---|
| 3,066,023 | 11/1962 | Schlesinger ........................... | 430/73 |
| 3,142,658 | 7/1964 | Stewart ............................ | 564/250 X |
| 3,290,147 | 12/1966 | Mattor et al. .................... | 564/249 X |
| 3,769,432 | 10/1973 | Tomenfcik ....................... | 564/251 X |
| 4,150,987 | 4/1979 | Anderson et al. ..................... | 430/58 |
| 4,278,747 | 7/1981 | Murayama et al. .............. | 430/58 X |
| 4,297,426 | 10/1981 | Sakai et al. ........................ | 430/58 X |
| 4,330,388 | 7/1982 | Sakai et al. ........................ | 430/58 X |
| 4,359,515 | 11/1982 | Katagiri et al. ................... | 430/78 X |

FOREIGN PATENT DOCUMENTS 56-65855 6/1981 Japan .................................. 564/249

*Primary Examiner*—Roland E. Martin, Jr.

*Attorney, Agent, or Firm*—Fitzpatrick, Cella, Harper & Scinto

[57] ABSTRACT

An electrophotographic photosensitive member is characterized by having a layer containing at least one of hydrazone group compounds represented by the following formula (1) or of ketazine group compounds represented by the following formula (2):

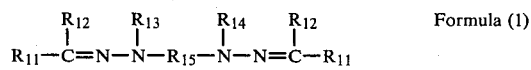

Formula (1)

In the formula, $R_{11}$ and $R_{12}$ independently of one another represent hydrogen, substituted or unsubstituted aryl, or substituted or unsubstituted heterocyclic radical; $R_{13}$ and $R_{14}$ independently of one another represent subsituted or unsubstituted alkyl, substituted or unsubstituted aralkyl, substituted or unsubstituted aryl, or substituted or unsubstituted heterocyclic radical; and $R_{15}$ represents a divalent organic residue.

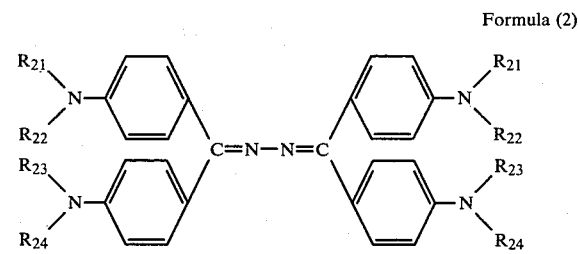

Formula (2)

In the formula, $R_{21}$, $R_{22}$, $R_{23}$, and $R_{24}$ independently one another represent substituted or unsubstituted alkyl, substituted or substituted aralkyl, or substituted or unsubstituted aryl, or $R_{21}$ and $R_{22}$, together with the nitrogen which links them, represent cyclic amino radical, and $R_{23}$ and $R_{24}$, together with the nitrogen which links them, represent cyclic amino radical.

42 Claims, No Drawings

ELECTROPHOTOGRAPHIC MEMBER WITH HYDRAZONE OR KETAZINE COMPOUNDS

BACKGROUND OF THE INVENTION

1. Field of the Invention

This invention relates to electrophotographic photosensitive members and more particularly to an electrophotographic photosensitive member having a photosensitive layer containing a novel organic photoconductive material comprising a hydrazone group compound or a ketazine group compound.

2. Description of the Prior Art

There have so far been known inorganic photoconductive materials such as selenium, cadmium sulfide, zinc oxide, etc. as photoconductive materials used for electrophotographic photosensitive members. In contrast to their many advantages, for instance, chargeability to a suitable potential in a dark place, slight dissipation in a dark place, and capability of dissipating rapidly charge by light irradiation, these photoconductive materials have various disadvantages, for example, as follows: in the case of selenium type photosensitive members, the crystallization of the photoconductive materials readily proceeds under the influence of surrounding factors such as temperature, moisture, dust, and pressure, in particular remarkably when the surrounding temperature exceeds 40° C., thus resulting in lowering of chargeability or white spots in image. In the case of these photosensitive members and cadmium sulfide type photosensitive members, stable sensitivity and durability cannot be obtained in repeated operations under high humidity conditions. In the case of zinc oxide type photosensitive members, which require sensitization by a sensitizing pigment, Rose Bengal being a typical sensitizing pigment, stable images cannot be obtained over a long period of time, since the sensitizing pigment tends to cause charge deterioration by corona discharge and light fading by exposure to light.

On the other hand, various kinds of organic photoconductive polymers have been proposed the first of which was polyvinylcarbozole. However, although excellent in film forming property, in lightness, and in some other points as compared with said inorganic photoconductive materials, these polymers have until now failed to be put to practical use, by reason that they are still unsatisfactory in film forming property and inferior to the inorganic photoconductive materials in sensitivity, durability, and stability to changes of environmental conditions.

In addition, the following low-molecular organic photoconductive materials have been offered:
1-Phenyl-3-(p-diethylaminostyryl)-5-(p-diethylaminophenyl)pyrazoline (U.S. Pat. No. 3,837,851, etc.), hydrazones (U.S. Pat. No. 4,150,987, etc.), 9-styrylanthracenes (Japan Pat. Appl. Laid-open Nos. 94828/1976 and 94829/1976, etc.), 4-chlorooxazoles (Japan Pat. Appl. Laid-open No. 53278/1980, etc.), 2-aza-q-fluorenones (Japan Pat. Appl. Laid-open No. 71236/1973, etc.), bis(p-dialkylaminostyryl)phenyls (Japan Pat. Appl. Laid-open No. 31773/1975, etc.), 2,6-bisstyrylpyridines (Japan Pat. Appl. Laid-open No. 94828/1976, etc.), spiro-pyrazolines (Japan Pat. Appl. Laid-open No. 112637/1979), N-(p-dialkylaminophenyl)carbazoles (Japan Pat. Appl. Laid-open No. 119925/1979, etc.), 2,5-bis (p-dialkylaminophenyl)-1,3,4-oxadiazoles (Japan Pat. Appl. Laid-open No. 121742/1979, etc.), bis (p-dialkyl-aminophenyl)alkanes (Japan Pat. Appl. Laid-open No. 17105/1980, etc.), and bis(p-dialkylaminophenyl)-quinolynoalkanes (Japan Pat. Appl. Laid-open No. 108667/1980 etc.).

Using proper binders, these low-molecular organic photoconductive materials have been able to solve the disadvantage of deficiency in film forming property, which is a problem of organic photoconductive polymers. However, the low-molecular organic photoconductive materials are still unsatisfactory with respect to sensitivity.

SUMMARY OF THE INVENTION

An object of this invention is to provide a novel electrophotographic photosensitive member free from the drawbacks or disadvantages described above.

Another object of the invention is to provide a novel organic photoconductive material.

Still another object of the invention is to provide a suitable charge-transporting compound for use in photosensitive layers of laminate structure comprising a charge generation layer and a charge transport layer.

According to the present invention, there is provided an electrophotographic photosensitive member characterized by having a layer containing at least one of hydrazone group compounds represented by the following formula (1) or of ketazine group compounds represented by the following formula (2):

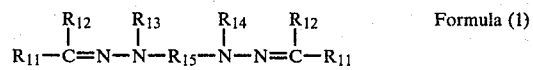

Formula (1)

wherein $R_{11}$ and $R_{12}$ independently of one another represent hydrogen, substituted or unsubstituted aryl, or substituted or unsubstituted heterocyclic radical; $R_{13}$ and $R_{14}$ independently of one another represent substituted or unsubstituted alkyl, substituted or unsubstituted aralkyl, substituted or unsubstituted aryl, or substituted or unsubstituted heterocyclic radical; and $R_{15}$ represents a divalent organic residue;

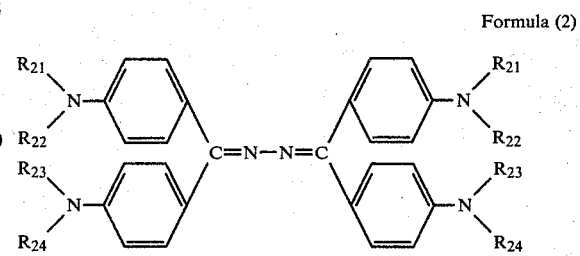

Formula (2)

wherein $R_{21}$, $R_{22}$, $R_{23}$, and $R_{24}$ independently of one another represent substituted or unsubstituted alkyl, substituted or unsubstituted aralkyl, or substituted aryl, or $R_{21}$ and $R_{22}$, together with the nitrogen which links them, represent cyclic amino radical, and $R_{23}$ and $R_{24}$, together with the nitrogen which links them, represent cyclic amino radical.

DETAILED DESCRIPTION

The specific hydrazone group and ketazine group compounds used in this invention can be represented by the following formulas (1) and (2), respectively:

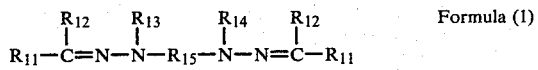

Formula (1)

In the formula, $R_{11}$ and $R_{12}$ independently of one another represent hydrogen, aryl (e.g., phenyl, naphthyl, anthryl, etc.), or heterocyclic radical (monovalent heterocyclic radical derived from, e.g., pyridine, quinoline, carbazole, phenothiazine, phenoxazine, etc.), wherein said aryl and heterocyclic radical also can have substituents. Said aryl is preferred to be substituted by disubstituted amino group (e.g., dialkylamino such as dimethylamino; diethylamino, dipropylamino, dibutylamino, and the like, or diarylamino such as dibenzylamino, diphenethylamino, ditolylamino, dixylylamino, and the like), cyclic amino group (e.g. morpholino, pyrrolidino, piperidino, and the like), or alkoxy group (e.g. methoxy, ethoxy, propoxy, butoxy, and the like), in particular at the 4-position when said aryl is phenyl or naphthyl. Alternatively, said aryl and heterocyclic radical can be substituted by alkyl (e.g., methyl, ethyl, n-propyl, isopropyl, n-butyl, t-butyl, n-amyl, t-amyl, etc.), halogen (e.g. chlorine, bromine, or iodine).

$R_{13}$ and $R_{14}$ independently of one another represent substituted or unsubstituted alkyl (e.g., methyl, ethyl, n-propyl, isopropyl, n-butyl, sec-butyl, t-butyl, n-amyl, t-amyl, 1,3-dimethylbutyl, n-octyl, 2-ethylhexyl, t-octyl, 2-hydroxyethyl, 3-hydroxypropyl, 2-chloroethyl, 3-chloropropyl, 2-methoxyethyl, 3-methoxypropyl, etc.), substituted or unsubstituted aralkyl (e.g., benzyl, phenethyl, chlorobenzyl, dichlorobenzyl, methoxybenzyl, α-naphthylmethyl, β-naphthylmethyl, etc.), substituted or unsubstituted aryl (e.g., phenyl, tolyl, xylyl, diphenyl, chlorophenyl, dichlorophenyl, trichlorophenyl, methoxyphenyl, dimethoxyphenyl, cyanophenyl, α-naphthyl, β-naphthyl, etc.), or substituted or unsubstituted heterocyclic radical (monovalent heterocyclic radical derived from, e.g., pyridine, quinoline, carbazole, phenothiazine, phenoxazine, etc. which may be substituted by alkyl such as methyl, ethyl, propyl, butyl, or amyl, and the like; halogen such as chlorine, bromine, and the like; alkoxy such as methoxy, ethoxy, propoxy, butoxy, and the like; cyano and the like).

$R_{15}$ represents a divalent organic residue, including divalent hydrocarbon residues, e.g., alkylenes such as methylene, ethylene, propylene, butylene, and the like, and arylenes such as phenylene, naphylene, biphenylene, and the like; divalent heterocyclic radicals derived from pyridine, quinoline, carbozole, phenothiazine, phenoxazine, and the like; and the following residues:

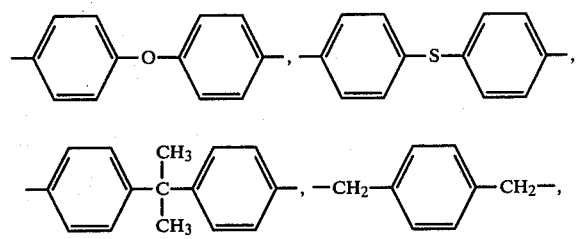

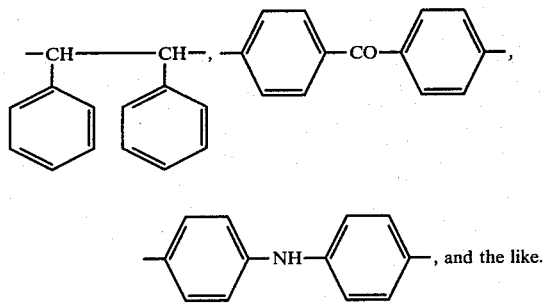

These divalent organic residues can be substituted by alkyl (e.g., methyl, ethyl, propyl, butyl, amyl, octyl, and the like), halogen (e.g., chlorine, bromine, iodine, and the like), alkoxy (e.g., methoxy, ethoxy, propoxy, butoxy, and the like), nitro, cyano, substituted amino (e.g., dimethylamino, diethylamino, dipropylamino, dibutylamino, dibenzylamino, diphenylamino, and the like), acylamino (e.g., acetylamino, propionylamino, butyrylamino, benzoylamino, toluoylamino, and the like), hydroxyl, carboxyl, sulfo, and the like.

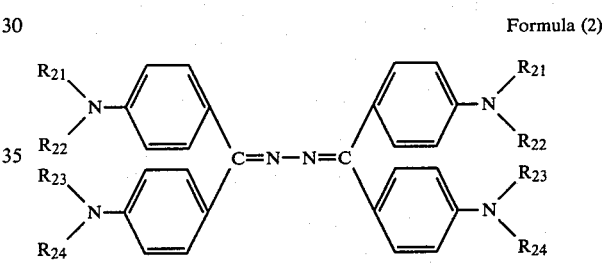

Formula (2)

In the formula, $R_{21}$, $R_{22}$, $R_{23}$, and $R_{24}$ independently of one another represent linear or branched alkyl such as methyl, ethyl, propyl, butyl, amyl, octyl, and the like; aralkyl such as benzyl, phenethyl, and the like; or aryl such as phenyl, tolyl, xylyl, α-naphthyl, β-naphthyl, and the like. The combination of $R_{21}$ and $R_{22}$, together with the nitrogen which links them and the combination of $R_{23}$ and $R_{24}$, together with the nitrogen which links them can form each a cyclic amino group, for example, morpholino, pyrrolidino, piperidino, and the like. Said alkyl, aralkyl, aryl, and cyclic amino group also can be substituted by alkoxy (e.g., methoxy, ethoxy, propoxy, butoxy, and the like), dialkylamino (e.g., dimethylamino, diethylamino, dipropylamino, dibutylamino, and the like), diaralkylamino (e.g. dibenzylamino, diphenethylamino, and the like), diarylamino (e.g., diphenylamino, ditolylamino, dixylylamino, and the like), or halogen (e.g. chlorine, bromine iodine, and the like). Further, said aralkyl and cyclic amino group can also substituted by alkyl such as methyl, ethyl, propyl, butyl, and the like.

Examples of the hydrazone group compounds represented by the above-mentioned formula (1) will be given below:

| Compound No. | |
|---|---|
| H-1 | 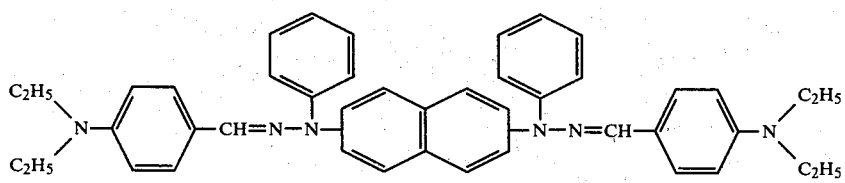 |
| H-2 | 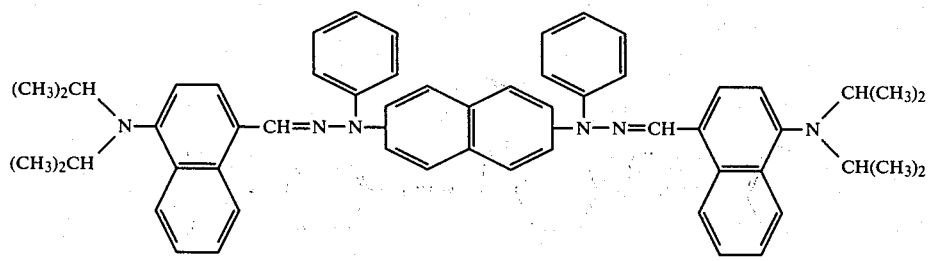 |
| H-3 | 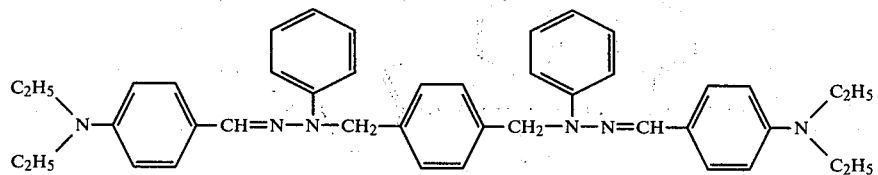 |
| H-4 | 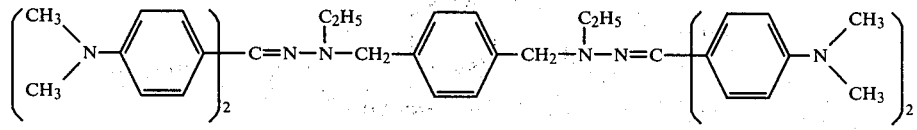 |
| H-5 | 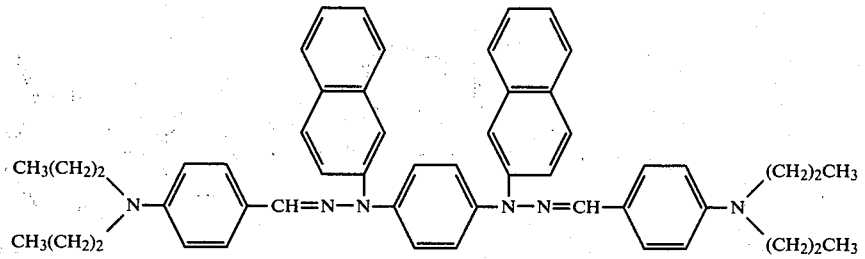 |
| H-6 | 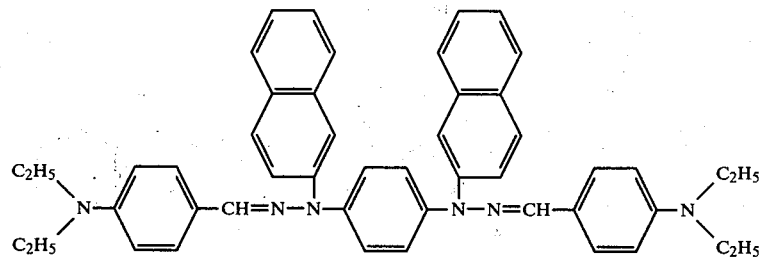 |
| H-7 | 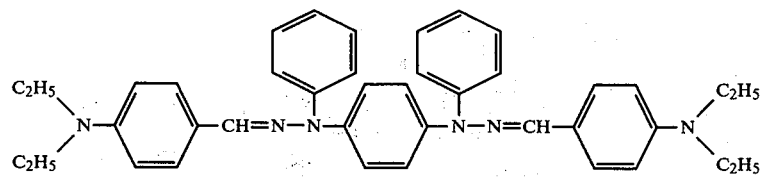 |

| Compound No. | |
|---|---|
| H-8 | 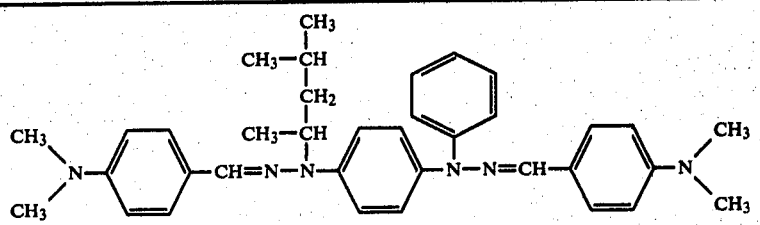 |
| H-9 | 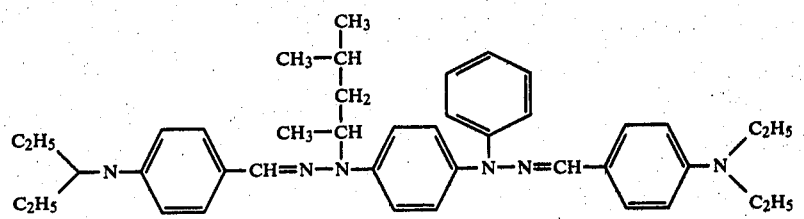 |
| H-10 | 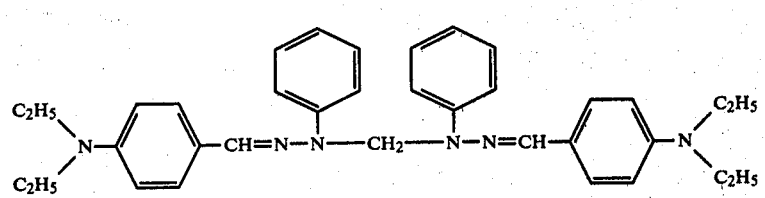 |
| H-11 | 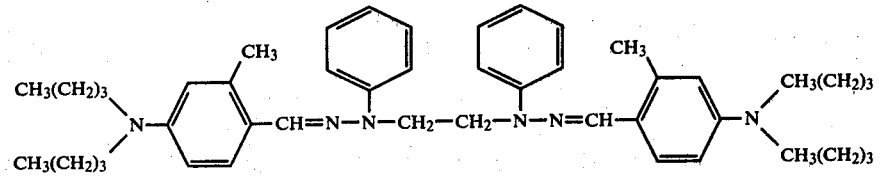 |
| H-12 | 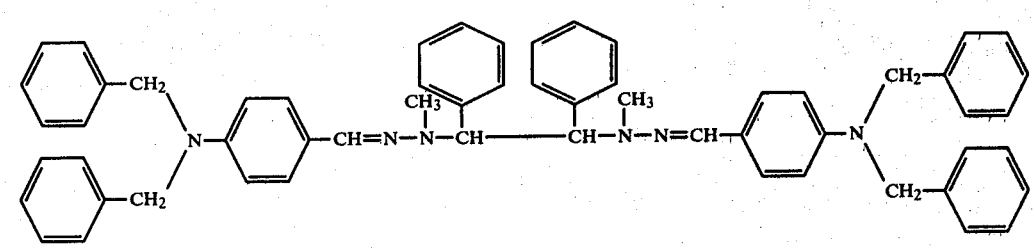 |
| H-13 | 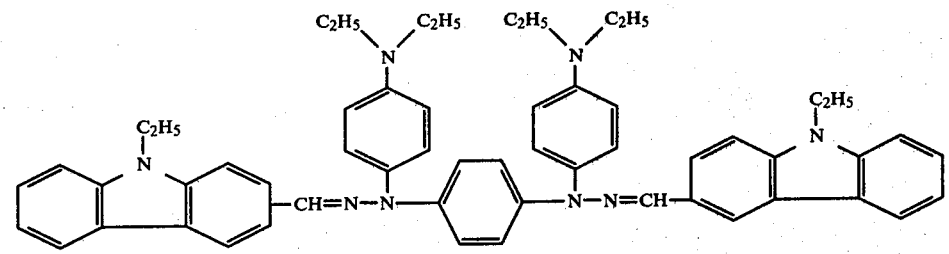 |
| H-14 | 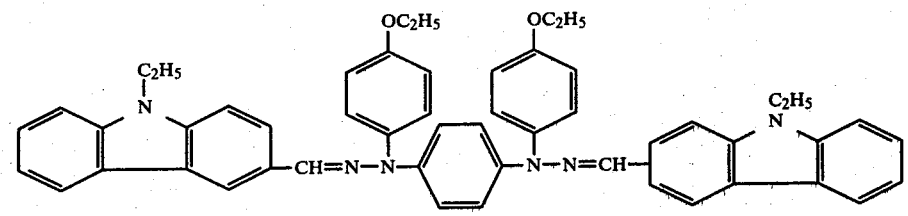 |

-continued
| Compound No. | |
|---|---|
| H-15 | 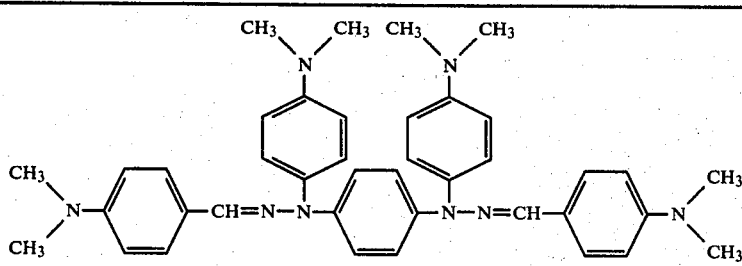 |
| H-16 | 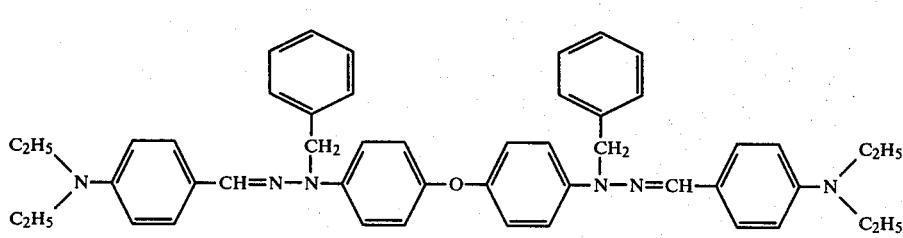 |
| H-17 | 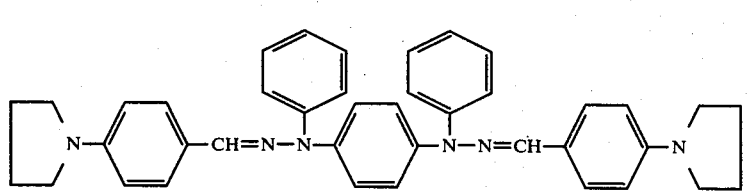 |
| H-18 | 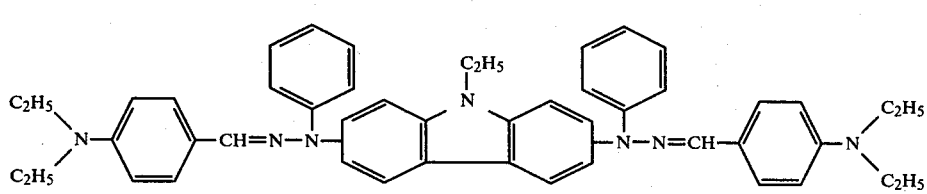 |
| H-19 | 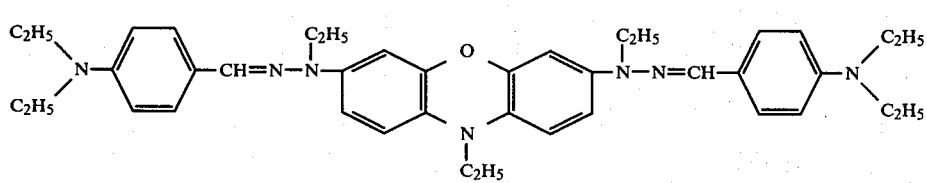 |
| H-20 | 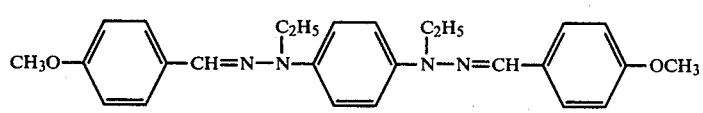 |
| H-21 | 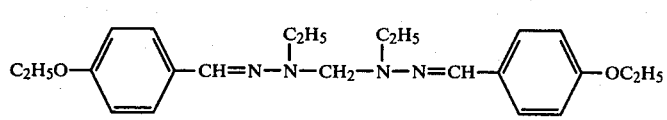 |
| H-22 | 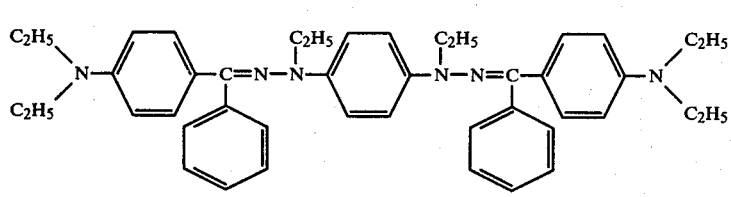 |

| Compound No. | |
|---|---|
| H-23 | 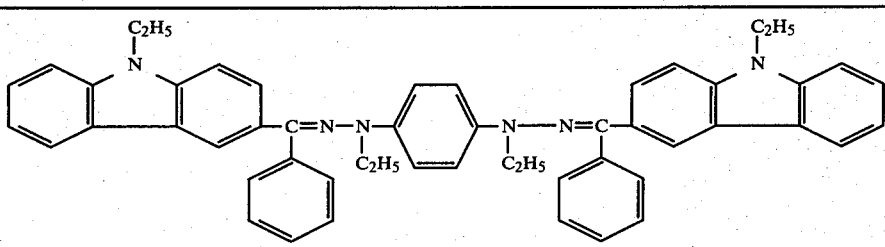 |
| H-24 | 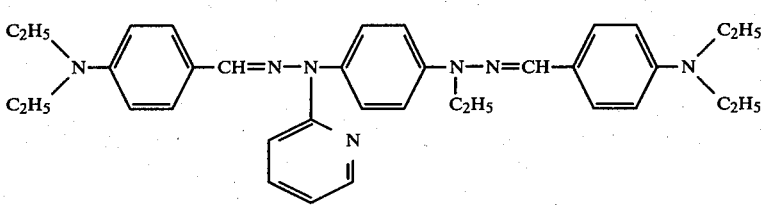 |
| H-25 | 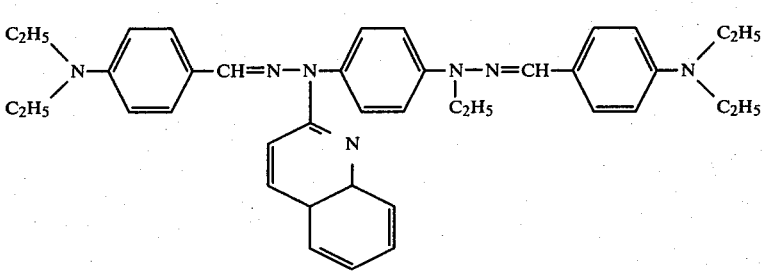 |
These compounds can be used alone or in combination with others. Examples of the ketazine group compounds represented by the above-mentioned formula (2) will be given below.
| No. | |
|---|---|
| K-1 | 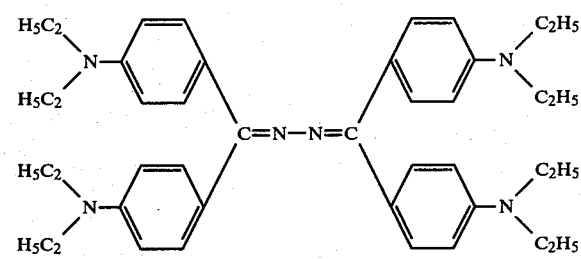 |
| K-2 | 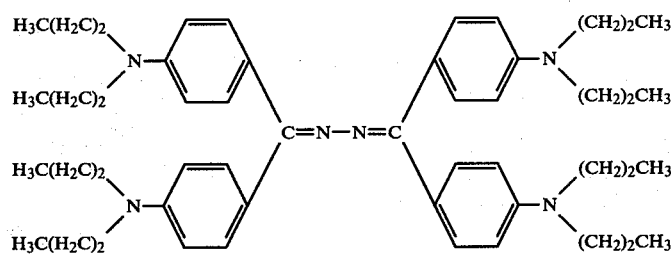 |

-continued
| No. |
|---|
K-3
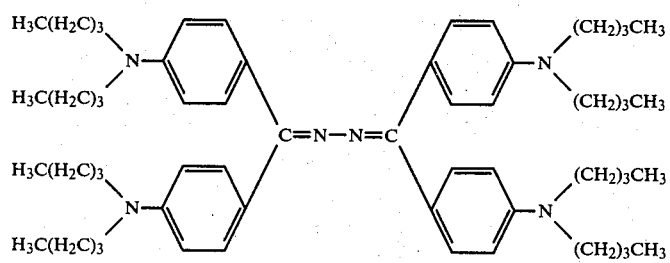
K-4
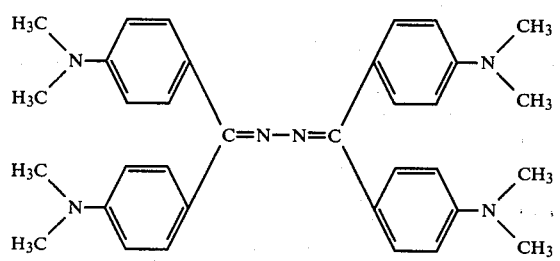
K-5
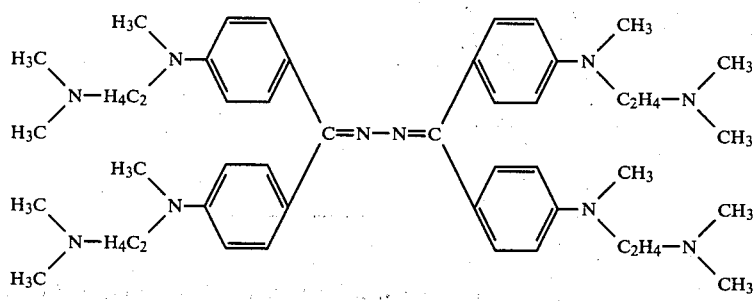
K-6
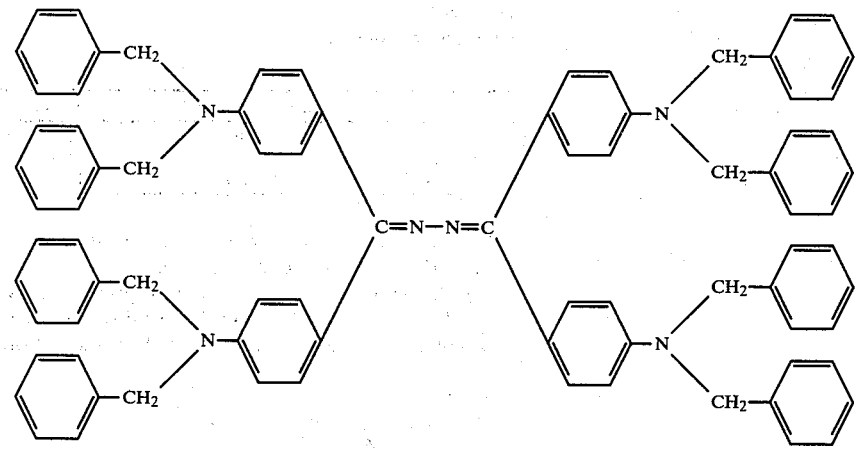
K-7
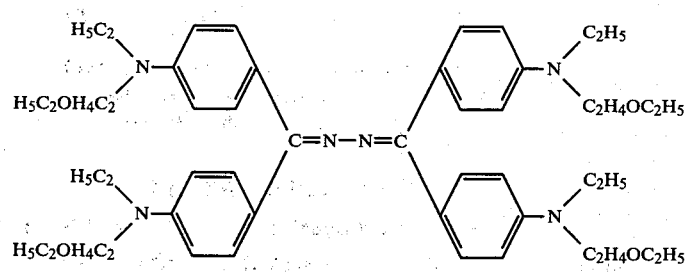

| No. | |
|---|---|
| K-8 | 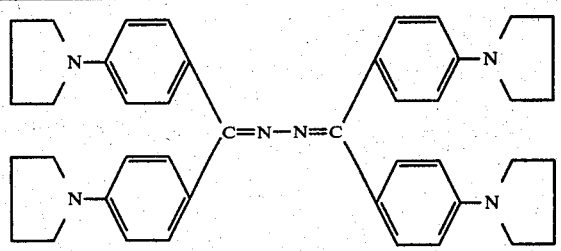 |
| K-9 | 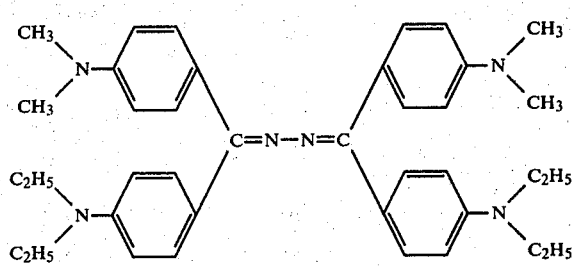 |
| K-10 | 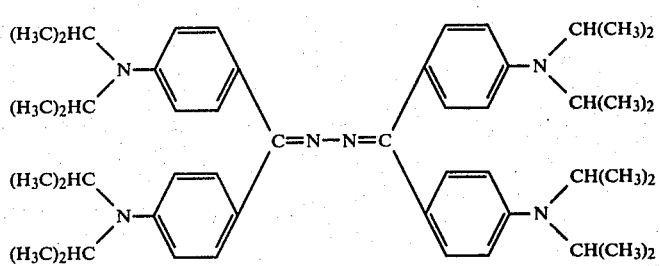 |

These compounds also can be used alone or in combination with others.

The hydrazone group compounds represented by formula (1) can be synthesized in the usual way by reacting a hydrazine represented by the formula

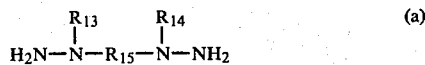

($R_{13}$, $R_{14}$, and $R_{15}$ are as defined above) with a carboxyl compound represented by the formula

($R_{11}$ and $R_{12}$ are as defined above).

An example of process for synthesizing a typical hydrazone group compound used in this invention will be illustrated below.

SYNTHESIS EXAMPLE 1

Synthesis of hydrazone group compound No. H-1

A mixture of 10.89 g (0.032 mol) of a hydrazine compound represented by formula (a) wherein $R_{13}$ and $R_{14}$ are each phenyl and $R_{15}$ is 2,7-naphthylene, 11.35 g (0.064 mol) of a carbonyl compound represented formula (b) wherein $R_{11}$ is p-diethylaminophenyl and $R_{12}$ is hydrogen, 100 ml of ethanol, and 100 ml of acetic acid was stirred for one hour to conduct reaction. The resulting solution was poured into water and the resulting precipitate was filtered off and dried. This cake was recrystallized from methyl ethyl ketone and 6.33 g of yellow crystal was obtained (m.p. 147.5°–150.0° C., yield 30%).

Elementary analysis:

| | Calcd. for $C_{44}H_{46}N_6$ | Found |
|---|---|---|
| C | 80.19% | 80.17% |
| H | 7.05% | 7.06% |
| N | 12.76% | 12.77% |

In similar ways, other hydrazone group compounds used in this invention can be synthesized.

The ketazine group compounds represented by formula (2) can be synthesized in the usual way by reacting hydrazine with a ketone represented by the formula

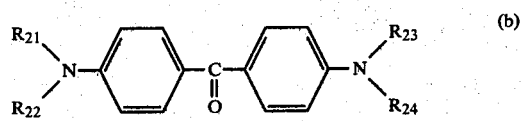

($R_{21}$, $R_{22}$, $R_{23}$ and $R_{24}$ are as defined above).

An example of process for synthesizing a ketazine group compound used in this invention will be illustrated below.

SYNTHESIS EXAMPLE 2

Synthesis of ketazine group compound No. K-1

In a 100-ml three-necked flask, 10.38 g (0.032 mol) of 4,4'-bis(diethylamino)benzophenone, 15 ml of acetic acid, and 1 g (0.016 mol) of hydrozine hydrate (80%) were placed and the reaction was carried out at 115° C. for 1 hour. The resulting liquid was cooled and poured into methanol. The resulting precipitate was filtered, washed with water, dried, and recrystallized from methyl ethyl ketone, and 2.48 g of orange coloured crystals was obtained (m.p. 207°–209° C., yield base on the ketone 24.0%).

Elementary analysis:

|   | Calcd. for $C_{42}H_{56}N_6$ | Found |
|---|---|---|
| C | 78.20% | 78.16% |
| H | 8.77% | 8.79% |
| N | 13.03% | 13.05% |

In similar ways, other ketazine group compounds used in this invention can be synthesized.

The hydrazone group and ketazine group compounds represented by formulas (1) and (2), respectively, can be applied to any type of electrophotographic photosensitive members using organic photoconductive materials, but the preferred types are as follows:

(1) A type containing a charge-transfer complex formed by combination of an electron donating substance and an electron accepting substance.

(2) A type containing an organic photoconductive material sensitized by addition of a dye.

(3) A type containing a hole matrix in which a pigment is dispersed.

(4) A type allotting functions to a charge generation layer and a charge transport layer.

(5) A type containing an organic photoconductive material and a co-crystalline complex of dye and resin as main components of the photosensitive layer.

(6) A type containing a charge-transfer complex to which an organic or inorganic charge-generating material has been added.

Of these types, (3) to (6) are particularly preferable. Moreover, when the present hydrazone group compounds represented by formula (1) or ketazine group compounds represented by formula (2) are applied to type (4), that is, applied as a charge-transporting material of the charge transport layer of a photosensitive member of type (4) wherein functions are alotted to the charge generation layer, the photosensitive member has improved sensitivity and lower residual potential. This is ascribed to effective transportation of the charge, generated in the charge generation layer, by the hydrazone or ketazine compounds contained in the charge transport layer which is laid in contiguity with the charge generation layer. In this case, the drop of sensitivity and the rise of residual potential in repeated operations can be depressed to a practically negligible level. Accordingly, photosensitive members of type (4) will be described below in detail.

A layer construction comprises essentially a conductive layer, a charge generation layer, and a charge transport layer, and the charge generation layer may be laid either above or below the charge transport layer, however, in the case of the photographic photosensitive member to be repeatedly used, the lamination in order of conductive layer, charge generation layer, and charge transport layer is preferred, chiefly in the aspect of physical strength and in certain cases in the aspect of charge bearing property. A bond layer may be laid, if necessary, between the conductive layer and the charge generation layer for the purpose of improving the adhesion between them.

The charge transport layer in this invention is preferably formed by coating a suitable solvent in which a hydrazone group compound represented by formula (1) or a ketazine group compound represented by formula (2) and a binder have been dissolved, and drying the coating. The binders usable in this case include, for example, polysulfone, acrylic resins, methacrylic resins, vinyl chloride resin, vinyl acetate resin, phenolic resins, epoxy resins, polyesters, alkyd resins, polycarbonates, polyurethan and copolymers containing two or more kinds of repeating units of these resins. In particular, polyesters and polycarbonates are preferable. Photoconductive polymers, such as poly(N-vinylcarbazole), having a charge-transporting function can also be used as the binder.

The mixing ratio of binder to charge-transporting compound is desirable to 100 parts by weight 10–500 parts by weight. Thickness of the charge transport layer is generally 2–100μ, preferably 5–30μ. For coating to form the charge transport layer, usual methods can be used such as blade coating, Meyer-bar coating, spray coating, dip coating, bead coating, air knife coating, and curtain coating.

A wide variety of organic solvents can be used for the coating solution for forming the charge transport layer of this invention. Typical examples thereof are aromatic hydrocarbons such as benzene, toluene, xylene, mesitylene, chlorobenzene, and the like; ketones such as acetone, 2-butanone, and the like; halogenated aliphatic hydrocarbons such as methylene chloride, chloroform, ethylene chloride, and the like; cyclic or linear ethers such as tetrahydrofuran, ethyl ether, and the like; and mixtures of these solvents.

The charge transport layer in this invention can also contain a variety of additives such as, for example, diphenyl, chlorinated diphenyl, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiopropionate, 3,5-dinitrosalicylic acid, fluorocarbons, silicone oil, silicone rubber, and further phenolic compounds such as dibuthylhydroxytoluene, 2,2'-methylene-bis-(6-t-butyl-4-methylphenol), α-tocopherol, 2-t-octyl-5-chlorohydroquinone, and 2,5-di-t-octylhydroquinone.

Any substance can be used as a charge-generating material of the charge generation layer, provided that it can absorb light and thereby generate charge-carriers in a highest efficiency. Preferred materials thereof include inorganic substances such as selenium, selenium-tellurium, selenium-arsenic, cadmium sulfide, amorphous silicon, and the like, and organic substances such as pyrylium dyes, thiopyrylium dyes, triarylmethane dyes, thiazine dyes, cyanine dyes, phthalocyanine pigments, perylene pigments, indio pigments, thioindigo pigments, quinacridone pigments, squaric acid pigments, azo pigments, polycyclic quinone pigments, and the like. Thickness of the charge generation layer is desirably up to 5μ, preferably 0.05–3μ.

Typical examples of the charge-generating material used in this invention are shown below.

Charge-generating material
(1) Amorphous silicon
(2) Selenium-tellurium
(3) Selenium-arsenic
(4) Cadmium sulfide (5) 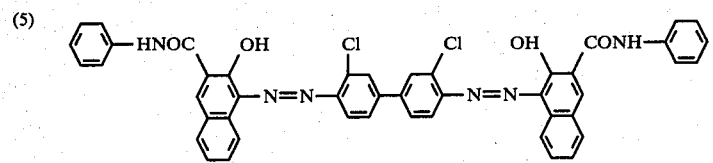
(6) 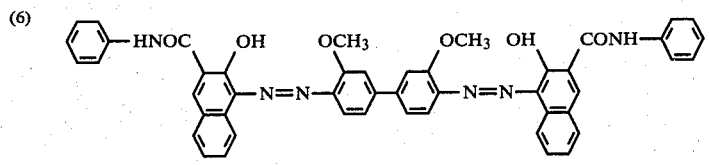
(7) 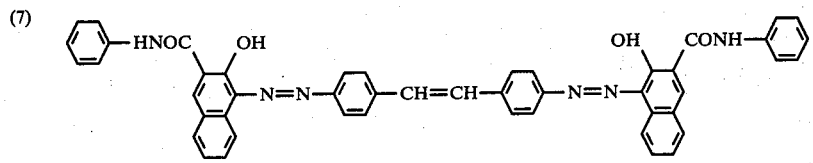
(8) 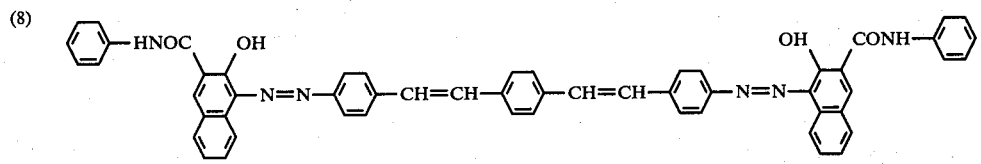
(9) 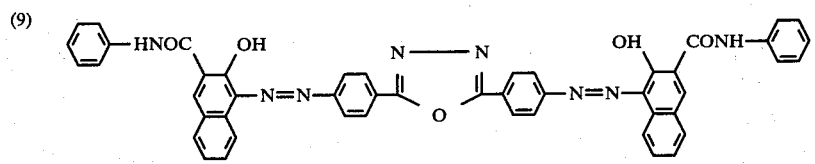
(10) 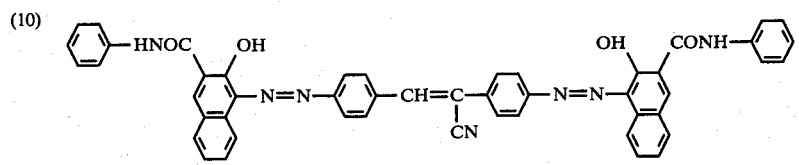
(11) 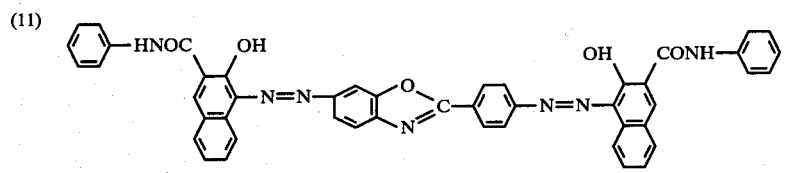
(12) 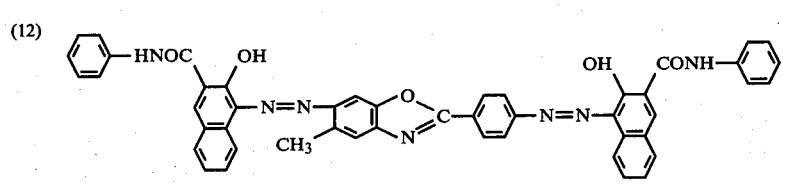
(13) 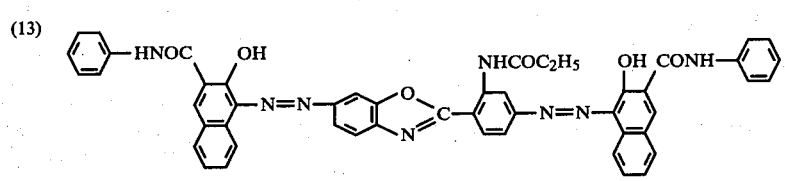

(14) 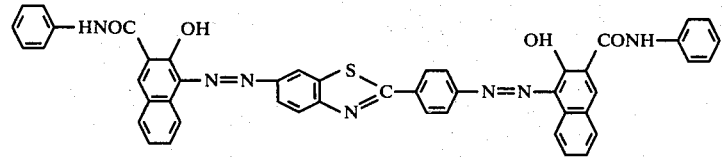
(15) 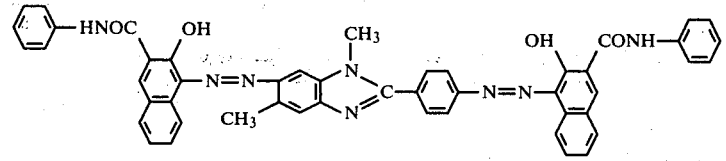
(16) 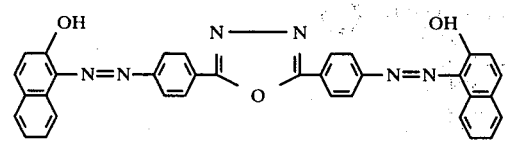
(17) 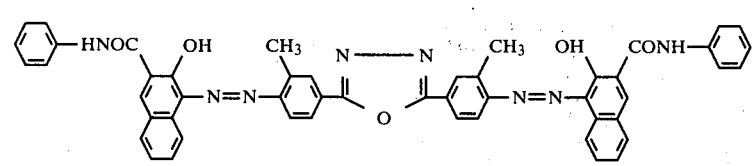
(18) 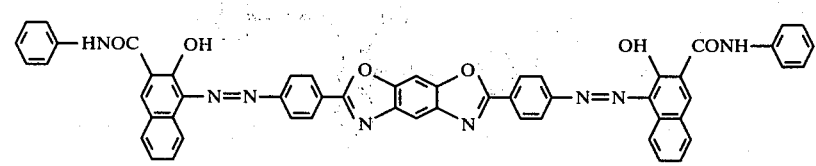
(19) 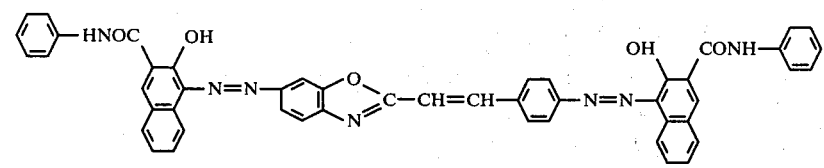
(20) 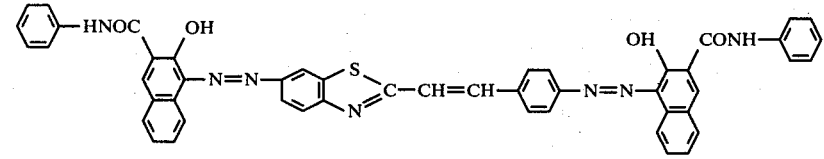
(21) 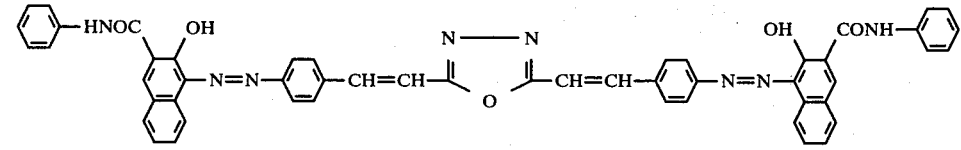
(22) 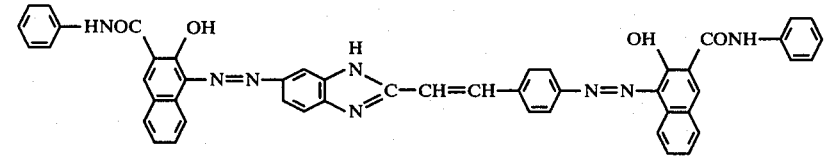

-continued
(23) 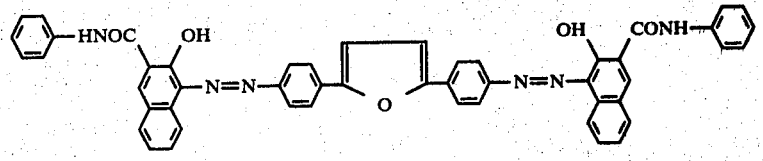
(24) 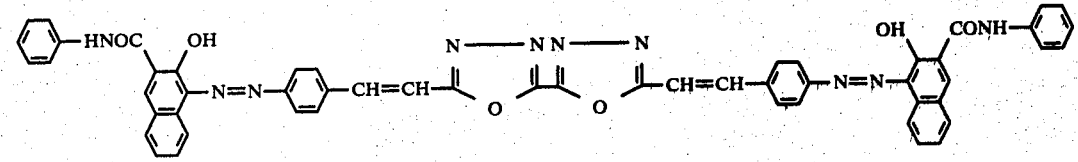
(25) 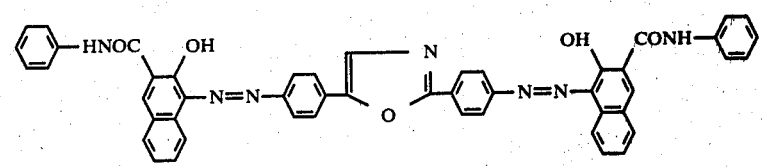
(26) 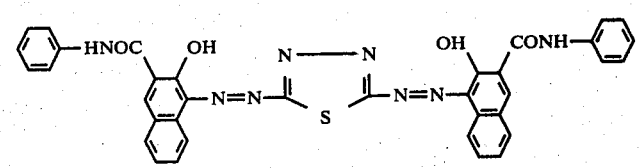
(27) 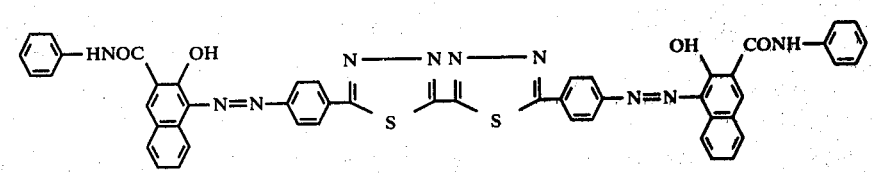
(28) 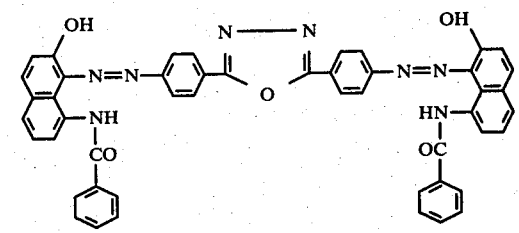
(29) 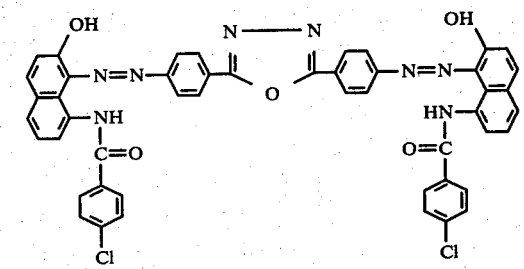
(30) 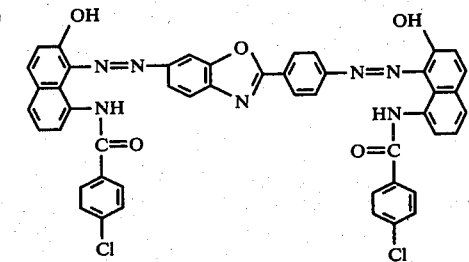

(31) 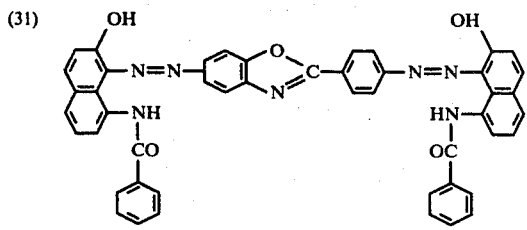
(32) 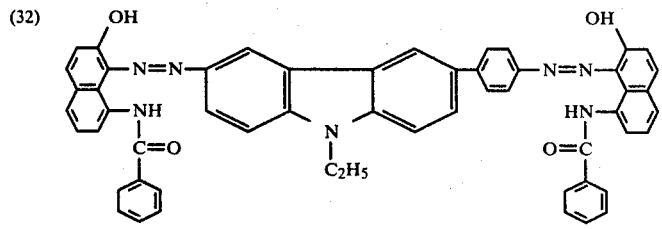
(33) 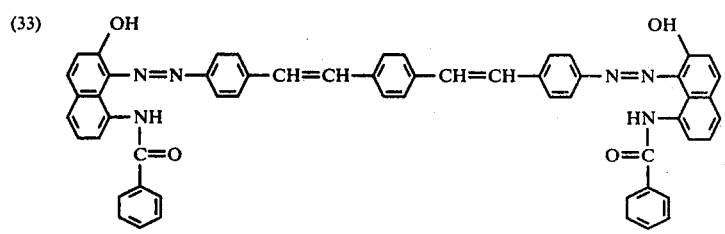
(34) 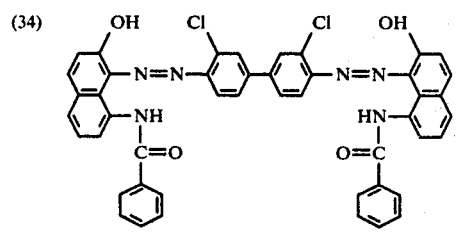
(35) 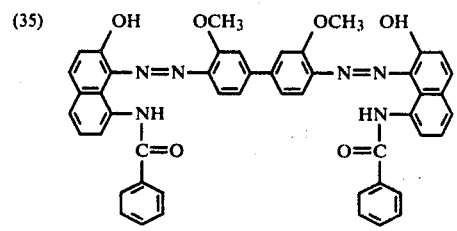
(36) 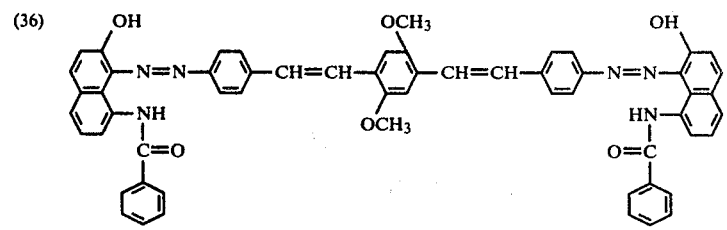
(37) 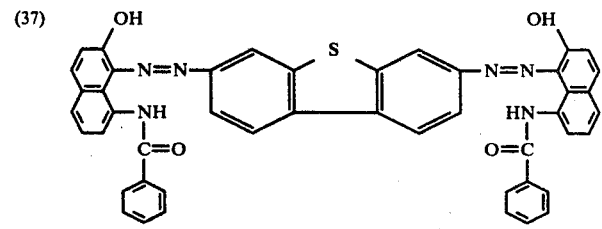

(38) 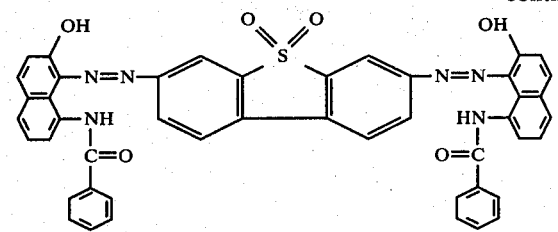
(39) 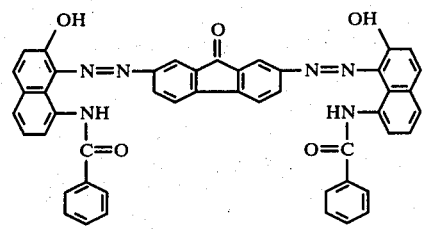
(40) 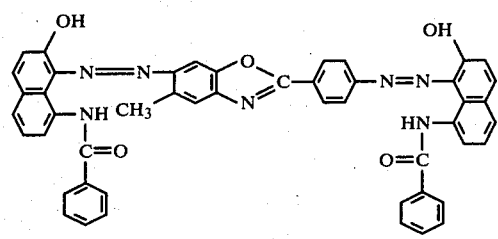
(41) 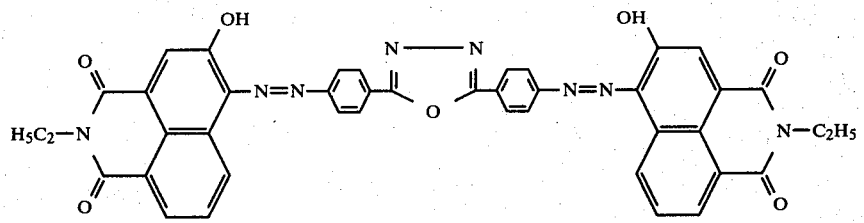
(42) 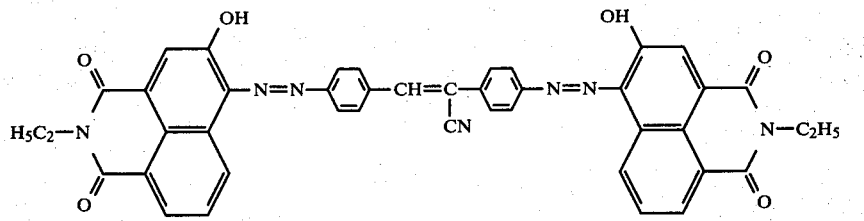
(43) 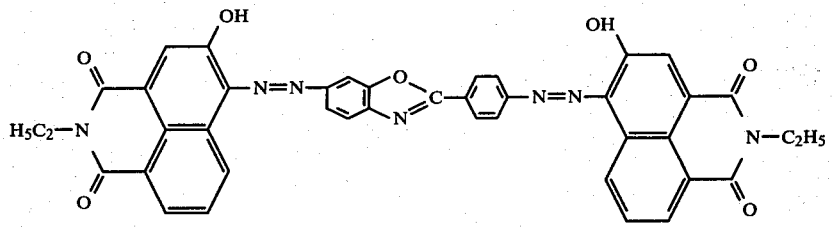
(44) 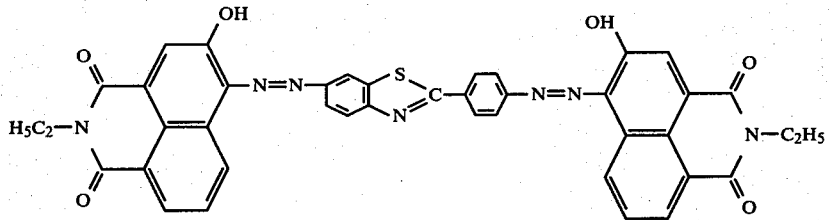

-continued

(45) 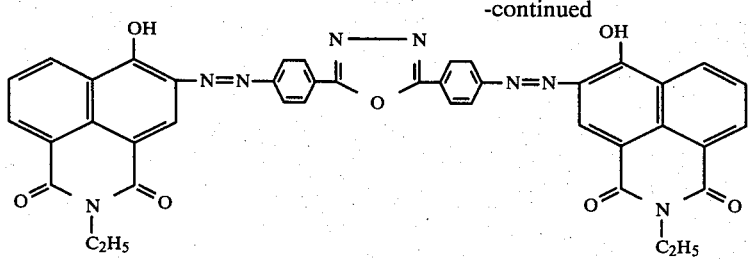

(46) 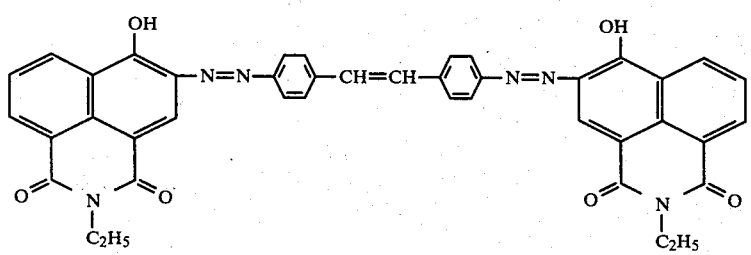

(47) 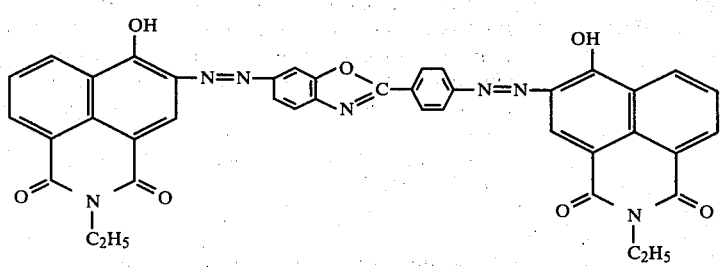

(48) 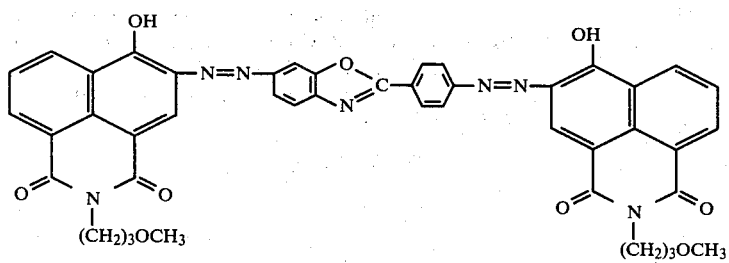

(49) 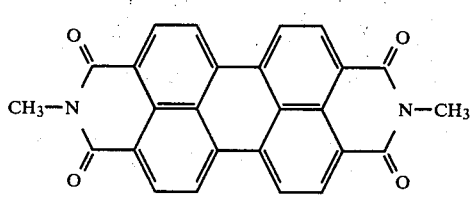

(50) 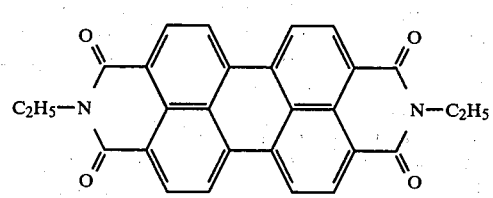

(51) Methine dyes derived from squaric acid
(52) Indigo dyes (C, I, No. 78000)
(53) Thioindigo dyes (C, I, No. 78800)
(54) Copper-phthalocyanines These pigments or dyes can be used alone or in combination with others. The crystal form of these pigments may be α-type, β-type, or any other type, but β-type is especially preferable.

The formation of the charge generation layer by use of the above-mentioned pigments, in this invention, can be carried out by vacuum deposition, sputtering, or glow discharge, according to kinds of said pigments. It is also possible to form said layer, depending upon kinds of the pigment, by coating a dispersion of the pigment in a suitable binder solution in a suitable coating way. Alternatively, a layer of said pigment can also be formed without using a binder. The dispersion of pigment can be performed by known methods employing a ball mill, attritor, and the like. Particle size of the dispersion is usually up to 5μ, preferably 2μ, most preferably 0.5μ. Said pigments can also be coated after dissolved in an amine series solvent such as ethylenediamine, diethylenetriamine, tetraethylenepentamine, pentaethylenehexamine, diethylaminopropylamine, N-aminoethylpiperazine, benzyldimethylamine, α-methylbenzyldimethylamine, tridimethylaminomethylphenol, and the like. The coating can be practiced by usual coating methods such as blade coating, Meyer bar coating, spray coating, dip coating, bead coating, air knife coating, and curtain coating.

Thickness of the charge generation layer in this invention is usually 5μ or less, preferably 0.01–1μ.

The binders for use in said dispersion include poly(vinylbutyral), poly(methyl methacrylate), polyesters, poly(vinylidene chloride), polyamides, chlorinated rubbers, polyvinyltoluene, polystyrene, poly(vinyl chloride), ethylcellulose, polyvinylpyridine, styrene-maleic anhydride copolymer, and the like. The binder content in the charge generation layer is usually up to 80%, preferably 50%, by weight.

In order to make uniform the carrier injection into the charge transport layer laid above the charge generation layer in the electrophotographic photosensitive member of this invention, the upper surface of the charge generation layer may be polished to mirror finished surface, if necessary.

The conductive layer may be of any existing type as far as it has conductivity.

Various conventional binders can be used for the above-said bond layer material, including casein, poly(vinyl alcohol), nitrocellulose, hydroxymethylcellulose, and the like.

Thickness of the bond layer is usually 0.1–5μ, preferably 0.5–3μ.

The hydrazone group and ketazine group compounds used in this invention are hole-transporting materials, so that it is required to negatively charge the surface of charge transport layer when using a photosensitive member having the construction laminated in order of conductive layer, charge generation layer, and charge transport layer. On exposing the charged photosensitive member to a pattern of light, holes generated in the charge generation layer of the exposed portions will be injected into the charge transport layer, then arrive at the surface thereof, and neutralize negative charge to decay the surface potential, thus producing an electrostatic contrast between the exposed and unexposed portions.

For visualizing this electrostatic contrast or latent image, various conventional processes of development can be applied.

The present hydrazone group and ketazine group compounds and effective for photosensitive members of other than type 4), that is, those described in a number of patent publications and literatures hitherto presented, such as, for example, the following:

(a) A type containing an organic photoconductive material and a co-crystal-line complex of dye and resin as main components of the photosensitive layer (U.S. Pat. No. 3,684,502, etc.).

(b) A type containing a hole matrix in which a pigment is dispersed (Japan Pat. Appl. Laid-Open No. 18545/1972, etc.).

(c) A type containing an organic photoconductive material sensitized by addition of a dye (U.S. Pat. No. 3,832,172, etc.).

(d) A type containing a charge-transfer complex formed by combination of an electron donating substance and an electron accepting substance (Japan Pat. Pub. No. 16197/1968, etc.).

(e) A type containing a charge-transfer complex to which an organic or inorganic charge-generating material has been added (U.S. Pat. No. 3,775,105, etc.).

The electrophotographic photosensitive member of this invention can be utilized in not only electrophotographic copying machines but also a wide range of application fields such as those of laser printers, CRT printers, and electrophotographic printing plate making systems.

The present invention will be illustrated below by way of examples.

EXAMPLE 1

A solution of casein in aqueous ammonia (casein 11.2 g, 28% aqueous ammonia 1 g, water 222 ml) was coated by means of a Meyer bar on an aluminum plate and dried to form a bond layer of 1.0 g/m².

A dispersion of 5 g of a disazo pigment having the structure

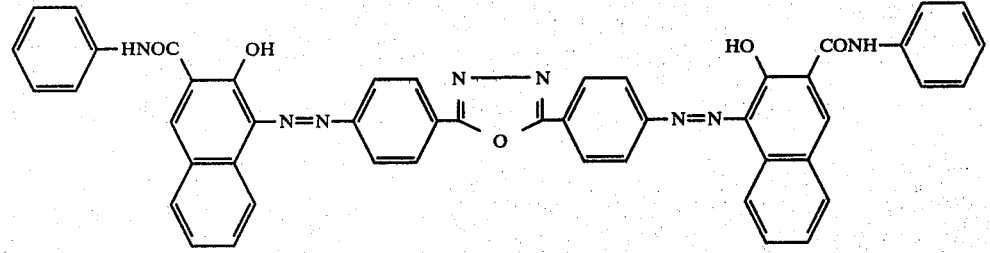

in a solution of 2 g of vinyl butyral resin (degree of butyral conversion: 63 mol%) in 95 ml of ethanol was coated on said bond layer to form a charge generation layer of 0.2 g/m² after drying.

A solution prepared by dissolving 5 g of the above-cited hydrazone compound (H-1) and 5 g of bisphenol A base polycarbonate (viscosity average mol.wt.: about 30,000) in 150 ml of dichloromethane was coated on said charge generation layer and dried to form a charge transport layer of 10 g/m².

The electrophotographic photosensitive member thus prepared was corona-charged at ⊖5 KV in the static state by using an electrostatic copying paper testing machine (Model SP-428, mfg. by Kawaguchi Denki K.K.), and after standing for 10 seconds in a dark place, was exposed to light at an intensity of 5 Lux to examine charge bearing characteristics.

The results were as follows, wherein Vo(V) is original potential, Rv is charge retention after standing for 10 seconds in a dark place, and El/2 (lux-sec) is exposure quantity for halving original potential:

Vo: ⊖480 V, Rv: 82%, El/2: 3.6 lux.sec

The measurements of charge bearing characteristics in the following examples were made in the same way as the above, unless otherwise noted.

EXAMPLES 2-18

The following pigment was vacuum deposited on aluminum plates each 100μ thick to form a charge generation layer of 0.15μ in thickness on each aluminum plate.

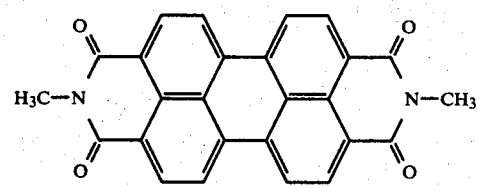

A solution prepared by dissolving 5 g of a polyester resin (Vylon 200, mfd. by Toyobo Co., Ltd.) and 5 g each of the above-mentioned hydrazone compounds (H-2 to H-18) in 150 ml of dichloromethane was coated on each charge generation layer and dried to form a charge transport layer.

Charge bearing characteristics of the electrophotographic members prepared in this way are shown in Table 1.

TABLE 1

| Example No. | Compound No. | Vo(−V) | Rv (%) | E½ (lux · sec) |
|---|---|---|---|---|
| 2 | H-2 | 460 | 81 | 3.9 |
| 3 | H-3 | 450 | 80 | 4.2 |
| 4 | H-4 | 440 | 79 | 4.0 |
| 5 | H-5 | 430 | 78 | 4.2 |
| 6 | H-6 | 440 | 78 | 3.8 |
| 7 | H-7 | 430 | 77 | 3.5 |
| 8 | H-8 | 460 | 82 | 4.6 |
| 9 | H-9 | 450 | 81 | 4.4 |
| 10 | H-10 | 490 | 84 | 5.8 |
| 11 | H-11 | 480 | 82 | 5.4 |
| 12 | H-12 | 500 | 87 | 6.7 |
| 13 | H-13 | 460 | 83 | 3.8 |
| 14 | H-14 | 480 | 84 | 4.1 |
| 15 | H-15 | 450 | 82 | 4.0 |
| 16 | H-16 | 490 | 86 | 6.6 |
| 17 | H-17 | 470 | 83 | 6.9 |
| 18 | H-18 | 460 | 80 | 4.1 |

EXAMPLE 19

Selenium-tellurium (tellurium 10 wt %) was vacuum deposited on an aluminum plate to form a charge generation layer of 0.8μ thickness.

Then, the same charge-transporting material as used in Example 1 was coated on said charge generation layer and dried to form a similar charge transport layer of 11 g/m².

Charge bearing characteristics of the electrophotographic photosensitive member thus prepared were as follows:

Vo: ⊖510 V, Rv: 82%, El/2: 2.7 lux.sec

EXAMPLE 20

After 1.0 g of β-type of copper-phthalocyanine was dispersed in a solution prepared by dissolving 5 g of the hydrazone compound (H-1), used also in Example 1, and 5 g of poly (N-vinylcarbazole) (mol. wt about 3.0×10⁵) in 150 ml of dichloromethane, the dispersion was coated on the same casein layer formed on the same aluminum plate as in Example 1, and dried to form a photosensitive layer of 10 g/m².

Charge bearing characteristics of the electrophotographic photosensitive member thus prepared were as follows: In this case the member was charged positively.

Vo: ⊕460 V, Rv: 79%, El/2: 16 lux.sec

EXAMPLE 21

A molybdenum plate (substrate), 0.2 mm thick, of which surface had been cleaned, was fixed at a definite position in a glow discharge vacuum deposition chamber. The chamber was evacuated to about $5 \times 10^{-6}$ torr. Thereafter, the input voltage of a heater was raised to heat the substrate and stabilize its temperature to 150° C. Then, a mixture of hydrogen gas and silane gas (15 vol% of hydrogen gas volume) was introduced into the chamber and the pressure in the chamber was stabilized at 0.5 torr by regulating the gas flow amount and the main valve of the chamber. High frequency power of 5 MHz was applied to an induction coil to generate glow discharge in a space in the chamber surrounded by the coil, where the input power was 30 W. Under these conditions, amorphous silicon film was developed on the substrate until the film thickness became 2μ, while keeping the same conditions. Then, the glow discharge was stopped, the heater and the high frequency power source were turned off, and after the substrate temperature was dropped to 100° C., the outflow valves of hydrogen gas and of silane gas were closed, the pressure in the chamber was once reduced to $10^{-5}$ torr and then returned to atmospheric pressure, and the substrate was taken out.

Subsequently, a charge transport layer was formed on the amorphous silicon layer in the same manner as Example 1.

The photosensitive member thus prepared was set in a charging and exposing test machine, corona-charged at ⊖6 KV, and immediately thereafter irradiated with a pattern of light which was made by passing the light from a tungsten lamp through a transmission type of test chart. Immediately after the irradiation, a positive charge developer (containing a toner and a carrier) was cascaded on the surface of the photosensitive member. Thus, a good toner image was obtained on the surface of the photosensitive member.

EXAMPLE 22

An electrophotographic photosensitive member was prepared in the same manner as Example 1, except that the above-mentioned ketazine compound (K-1) was used as a charge-transporting material in place of the hydrazone compound (H-1).

Charge bearing characteristics of the photosensitive member were as follows:

Vo: ⊖580 V, Rv: 93%, El/2 6.9 lux.sec

EXAMPLES 23-32

Electrophotographic photosensitive members were prepared in the same manner as Examples 2-18, except the above-mentioned ketazine compounds (K-1 to K-10) were severally used as charge-transporting materials in place of the hydrazone compounds.

Charge bearing characteristics of the photosensitive members are shown in Table 2.

TABLE 2

| Example No. | Compound No. | Charge bearing characteristics | | |
|---|---|---|---|---|
| | | Vo(−V) | Rv (%) | E½ (lux · sec) |
| 23 | K-1 | 580 | 91 | 7.1 |
| 24 | K-2 | 580 | 92 | 7.8 |
| 25 | K-3 | 600 | 90 | 8.7 |
| 26 | K-4 | 590 | 94 | 10.2 |
| 27 | K-5 | 610 | 93 | 9.1 |
| 28 | K-6 | 580 | 90 | 9.3 |
| 29 | K-7 | 590 | 91 | 8.0 |
| 30 | K-8 | 590 | 93 | 10.8 |
| 31 | K-9 | 600 | 93 | 8.3 |
| 32 | K-10 | 570 | 92 | 8.0 |

EXAMPLE 33

Selenium-tellurium (tellurium 10 wt%) was vacuum deposited on an aluminum plate to form a charge generation of 0.8μ thickness.

Then, a charge transport layer was formed on this charge generation layer in the same manner as Example 22, except that the thickness of the charge transport layer was 11 g/m².

Charge bearing characteristics of the electrophotographic member thus obtained were as follows:

Vo: ⊖570 V, Rv: 91%, E1/2: 5.8 lux.sec

EXAMPLE 34

An electrophotographic photosensitive member was prepared in the same manner as Example 20, except that the ketazine compound (K-1) was used in place of the hydrozone compound (H-1).

Charge bearing characteristics of the photosensitive member were as follows: In this case the member was charged positively.

Vo: ⊕510 V, Rv: 88%, E1/2: 14 lux.sec

EXAMPLE 35

On the amorphous silicon layer formed in Example 21, a charge transport layer was formed in the same manner as Example 22.

The photosensitive member thus prepared was tested in the same fashion as Example 21, and a good toner image was obtained thereon.

What we claim is:

1. An electrophotographic photosensitive member characterized by having a layer containing at least one of hydrazone group compounds represented by the following formula (1) or of ketazine group compounds represented by the following formula (2):

$$\begin{array}{cccc} R_{12} & R_{13} & R_{14} & R_{12} \\ | & | & | & | \\ R_{11}-C=N-N-R_{15}-N-N=C-R_{11} \end{array}$$ Formula (1)

wherein $R_{11}$ and $R_{12}$ independently of one another are hydrogen, substituted or unsubstituted aryl, or substituted or unsubstituted heterocyclic radical; $R_{13}$ and $R_{14}$ independently of one another are substituted or unsubstituted alkyl, substituted or unsubstituted aralkyl, substituted heterocyclic radical; and $R_{15}$; is a divalent hydrocarbon radical which may be substituted, a divalent organic residue derived from a heterocyclic ring which may be substituted,

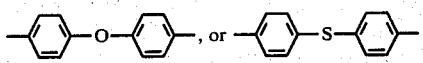

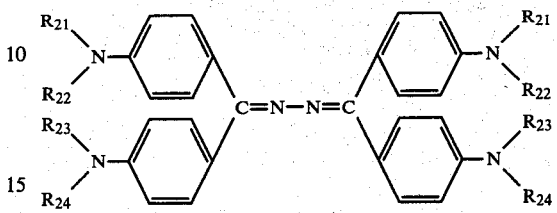

Formula (2)

wherein $R_{21}$, $R_{22}$, $R_{23}$, and $R_{24}$ independently of one another are substituted or unsubstituted alkyl, substituted or unsubstituted aralkyl, or substituted or unsubstituted aryl, or $R_{21}$ and $R_{22}$, together with the nitrogen which links them, is cyclic amino radical, and $R_{23}$ and $R_{24}$, together with the nitrogen which links them, is cyclic amino radical.

2. An electrophotographic photosensitive member according to claim 1, wherein $R_{11}$ is a radical selected from the group consisting of p-dialkylaminophenyl, p-di-aralkylaminophenyl, p-diarylaminophenyl, p-morpholinophenyl, p-piperidinophenyl, p-pyrrolidinophenyl, p-alkoxyphenyl, p-dialkylamino-1-naphthyl, and N-alkylcarbazolyl.

3. An electrophotographic photosensitive member according to claim 2, wherein $R_{11}$ is p-dialkylaminophenyl.

4. An electrophotographic photosensitive member according to claim 3, wherein $R_{11}$ is a radical selected from the group consisting of p-dimethylaminophenyl, p-diethylaminophenyl, p-dipropylaminophenyl, and p-dibutylaminophenyl.

5. An electrophotographic photosensitive member according to claim 4, wherein $R_{11}$ is p-diethylaminophenyl.

6. An electrophotographic photosensitive member according to any of claims 2–5, wherein $R_{12}$ is hydrogen.

7. An electrophotographic photosensitive member according to any of claims 2–5, wherein $R_{12}$ is substituted or unsubstituted aryl.

8. An electrophotographic photosensitive member according to claim 7, wherein said aryl is a radical selected from the group consisting of phenyl and p-dialkylaminophenyl.

9. An electrophotographic photosensitive member according to claim 1, wherein $R_{15}$ is a radical selected from the group consisting of from alkylene and arylene.

10. An electrophotographic photosensitive member according to claim 9, wherein $R_{15}$ is a radical selected from the group consisting of methylene, ethylene, p-phenylene, and 2,7-naphthylene.

11. An electrophotographic photosensitive member according to claim 1, wherein $R_{15}$ is a divalent organic residue selected from the group consisting of

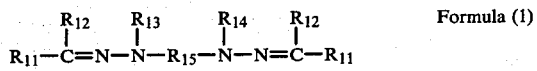

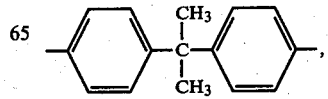

-continued

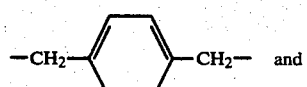

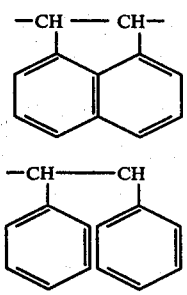

12. An electrophotographic photosensitive member according to claim 1, wherein $R_{15}$ is a divalent organic residue derived from a heterocyclic ring selected from the group consisting of pyridine, quinoline, carbazole, phenothiazine, and phenoxazine.

13. An electrophotographic photosensitive member according to claim 12, wherein $R_{15}$ is a divalent organic residue derived from N-ethylcarbazole.

14. An electrophotographic photosensitive member according to claim 1, wherein $R_{13}$ and $R_{14}$ are the same or different and each represents a radical selected from the group consisting of phenyl, p-dialkylaminophenyl, p-diaralkylaminophenyl, p-methoxyphenyl, naphthyl, methyl, ethyl, n-propyl, isopropyl, n-butyl, sec-butyl, t-butyl, 1,3-dimethylbutyl, benzyl, 2-pyridyl, and 2-quinolyl.

15. An electrophotographic photosensitive member according to claim 14, wherein, $R_{13}$ and $R_{14}$ are the same or different and each represents a radical selected from the group consisting of phenyl, p-dimethylaminophenyl, p-diethylaminophenyl, p-dibenzylaminophenyl, p-ethoxyphenyl, β-naphthyl, methyl, ethyl, and 1,3-dimethylbutyl.

16. An electrophotographic photosensitive member according to claim 15, wherein $R_{13}$ and $R_{14}$ are each phenyl.

17. An electrophotographic photosensitive member according to claim 15, wherein $R_{13}$ and $R_{14}$ are each p-diethylaminophenyl.

18. An electrophotographic photosensitive member according to claim 15, wherein $R_{13}$ and $R_{14}$ are each β-naphthyl.

19. An electrophotographic photosensitive member according to claim 15, wherein $R_{13}$ and $R_{14}$ are each methyl.

20. An electrophotographic photosensitive member according to claim 15, wherein $R_{13}$ and $R_{14}$ are each ethyl.

21. An electrophotographic photosensitive member according to claim 15, wherein $R_{13}$ is 1,3-dimethylbutyl and $R_{14}$ is phenyl.

22. An electrophotographic photosensitive member according to claim 1, wherein $R_{21}$, $R_{22}$, $R_{23}$, and $R_{24}$ are the same or different and each represents a radical selected from the group consisting of methyl, ethyl, n-propyl, n-butyl, benzyl, 2-dimethylaminoethyl, and 2-ethoxyethyl.

23. An electrophotographic photosensitive member according to claim 22, wherein $R_{21}$, $R_{22}$, $R_{23}$, and $R_{24}$ are each ethyl.

24. An electrophotographic photosensitive member according to claim 1, wherein $R_{21}$ and $R_{22}$, together with the nitrogen which links them, and $R_{23}$ and $R_{24}$, together with the nitrogen which links them, form each a ring selected from the group consisting of pyrrolidine, piperidine, and morpholine rings.

25. An electrophotographic photosensitive member according to claim 24, wherein the combination of neighboring $R_{21}$, $R_{22}$, and the nitrogen which links $R_{21}$ and $R_{22}$, and the combination of neighboring $R_{23}$, $R_{24}$, and the nitrogen which links $R_{23}$ and $R_{24}$ from each a pyrrolidine ring.

26. An electrophotographic photosensitive member according to claim 1, wherein said layer containing at least one of hydrazone group compounds or of ketazine group compounds has a function to transport the electric charge generated in a charge generation layer.

27. An electrophotographic photosensitive member according to claim 26, wherein said electric charge comprises holes.

28. An electrophotographic photosensitive member according to claim 26, wherein said layer containing at least one of hydrazone group compounds or of ketazine group compounds is laid in contiguity with the charge generation layer.

29. An electrophotographic photosensitive layer according to claim 28, wherein said layer containing at least one of hydrazone group compounds or of ketazine group compounds is laid above the charge generation layer.

30. An electrophotographic photosensitive layer according to claim 29, wherein said charge generation layer contains a compound selected from the group consisting of azo pigments, pyrylium dyes, thiopyrylium dyes, triarylmethane dyes, thiazine dyes, cyanine dyes, phthalocyanine dyes, indigo dyes, thioindigo dyes, quinacridone pigments, squaric acid pigments, and polycyclic quinone pigments.

31. An electrophotographic photosensitive member according to claim 30, wherein said charge generation layer comprises a bis-azo pigment and a binder.

32. An electrophotographic photosensitive member according to claim 30, wherein said charge generation layer comprises methine dyes derived from squaric acid and a binder.

33. An electrophotographic photosensitive member according to claim 30, wherein said charge generation layer comprises a vacuum deposition film of selenium-tellurium.

34. An electrophotographic photosensitive member according to claim 26, wherein said charge generation layer comprises an amorphous silicon film.

35. An electrophotographic photosensitive member according to claim 34, said amorphous silicon coat is a film formed by glow discharge.

36. An electrophotographic photosensitive member according to claim 26, wherein said charge generation layer comprises a vacuum deposition film of a perylene pigment.

37. An electrophotographic photosensitive member according to claim 26, wherein said charge generation layer is laid on a conductive layer.

38. An electrophotographic photosensitive member according to claim 37, wherein an intermediate layer is laid between said conductive layer and said charge generation layer.

39. An electrophotographic photosensitive member according to claim 1, wherein said layer containing at least one of hydrazone group compounds or of ketazine group compounds contains an organic photoconductive polymer and a charge-generating material.

40. An electrophotographic photosensitive member according to claim 39, wherein said photoconductive polymer is poly(N-vinylcarbazole).

41. An electrophotographic photosensitive member according to claim 39, which comprises at least one of said hydrazone group compounds or of said ketazine group compounds, a charge-generating material, and an organic photoconductive polymer.

42. An electrophotographic photosensitive member according to claim 41, wherein said photoconductive polymer is poly(N-vinylcarbazole).

* * * * *